United States Patent [19]

Houlihan

[11] 4,301,170
[45] Nov. 17, 1981

[54] 1-DIMETHYL SUBSTITUTED ALKYL-2-OR 4-SUBSTITUTED PHENYLIMIDAZOLES

[75] Inventor: William J. Houlihan, Mt. Lakes, N.J.

[73] Assignee: Sandoz, Inc., East Hanover, N.J.

[21] Appl. No.: 174,718

[22] Filed: Aug. 1, 1980

Related U.S. Application Data

[63] Continuation of Ser. No. 98,868, Nov. 30, 1979, abandoned, which is a continuation of Ser. No. 953,269, Oct. 20, 1978, abandoned, which is a continuation of Ser. No. 903,155, May 5, 1978, abandoned, which is a continuation-in-part of Ser. No. 861,993, Dec. 19, 1977, abandoned.

[51] Int. Cl.³ .................. A61K 31/415; C07D 233/58
[52] U.S. Cl. ............................. 424/273 R; 548/346;
548/335
[58] Field of Search .................. 424/273 R; 548/335, 548/346

[56] References Cited

U.S. PATENT DOCUMENTS 3,917,634  11/1975  Houlihan ........................... 548/346

FOREIGN PATENT DOCUMENTS 1486817  5/1967  France ............................. 548/335

OTHER PUBLICATIONS

Spaenig et al., Chem. Abst. 19629, 1966.
Holtschmidt et al., Chem. Abst. 85:5640y.
Edwards, Chem. Abst. vol. 79, 1973, 18714b.
Eq. to Fr. 1603793, Chem. Abst. vol. 76, 1972, 85820j.

Primary Examiner—Henry R. Jiles
Assistant Examiner—Jane T. Fan
Attorney, Agent, or Firm—Gerald D. Sharkin; Robert S. Honor; Timothy G. Rothwell

[57] ABSTRACT

This disclosure describes novel compounds of the formula

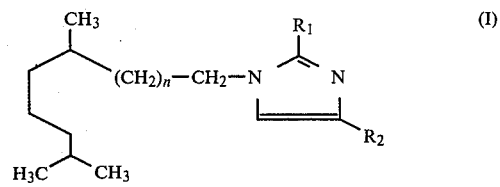

wherein
$R_1$ and $R_2$ each represent hydrogen, or

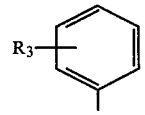

and
$R_3$ is hydrogen or fluoro, and
n is 1, 2 or 3, and
provided that one of $R_1$ and $R_2$ is other than hydrogen which are useful as anti-obesity agents.

9 Claims, No Drawings

1-DIMETHYL SUBSTITUTED ALKYL-2-OR 4-SUBSTITUTED PHENYLIMIDAZOLES

This is a continuation of application Ser. No. 98,868, filed Nov. 30, 1979 now abandoned, which in turn is a continuation of application Ser. No. 953,269, filed Oct. 20, 1978, now abandoned, which in turn is a continuation of application Ser. No. 903,155, filed May 5, 1978, now abandoned, which in turn is a continuation-in-part of Ser. No. 861,993, filed Dec. 19, 1977, now abandoned.

This application relates to 1-dimethyl-substituted alkyl-2- or 4-substituted phenylimidazoles which are useful as anti-obesity agents. In particular, it relates to 1-dimethyl-substituted alkyl-2- or 4-substituted-phenylimidazoles and their pharmaceutically acceptable acid addition salts.

The compounds of this invention may be represented by the following structural formula:

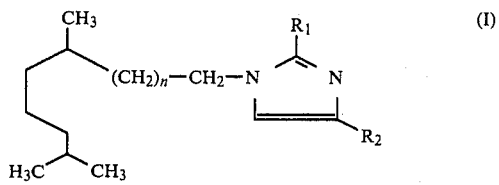

wherein
$R_1$ and $R_2$ each represent hydrogen, or

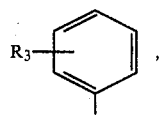

and
$R_3$ is hydrogen or fluoro, and
n is 1, 2 or 3, and
provided that one of $R_1$ and $R_2$ is other than hydrogen.

The compounds of formula (I) may be prepared according to the following reaction scheme:

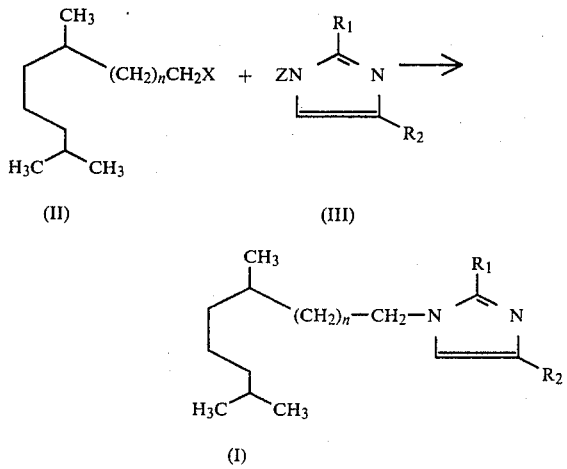

where
X is halo having an atomic weight of about 35 to 127 or

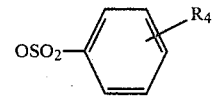

wherein
$R_4$ is hydrogen, chlorine, or methyl,
Z is sodium, potassium or lithium, and
$R_1$, $R_2$, n and the proviso are as defined above.

The compounds of formula (I) are prepared by treating a compound of the formula (II) with a compound of the formula (III) under an inert atmosphere preferably nitrogen in the presence of an inert organic solvent. Although the particular solvent employed is not critical, the preferred solvents include the aromatic hydrocarbons such as benzene, toluene and the like, the ethers such as dioxane, tetrahydrofuran and the like, dimethylacetamide and dimethylformamide, the latter being especially preferred. The temperature of the reaction is not critical, but it is preferred that the reaction be carried out between about 15° to 60° C., preferably from about 20° to 30° C. The reaction may be run from about 8 to 36 hours, preferably from about 12 to 20 hours. The product is recovered using conventional techniques, e.g., distillation or crystallization or when necessary, column chromatography followed by distillation or crystallization.

The compounds of formulae (II) and (III) are known and may be prepared by methods described in the literature.

It will be understood that the compounds of formula (I) may exist in the form of optically active isomers which can be separated and recovered by conventional techniques, and such isomeric forms are also included within the scope of this invention.

The compoounds of formula (I) are useful because they possess pharmacological activity in animals. In particular, the compounds of formula (I) are useful as anti-obesity agents in the treatment of obesity as indicated by preventing an increase in the blood sugar level in male Wistar rats in groups of 4 which are fasted for 16 hours and then are given an initial dose of 200 milligrams per kilogram of animal body weight of the test compound orally. One hour later, the rats are given 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxymethyl cellulose and are run concurrently. The blood sugar levels are calculated and compared to the control.

For such usage, the compounds of formula (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs, and parenterally as solutions, suspensions and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base and are readily prepared by reacting the base with an appropriate acid and accordingly, are included within the scope of this invention. Representative of such salts are the mineral acid salts such as the hydrochloride, hydrobromide, sulfate, phosphate and the like and the organic salts such as the succinate, benzoate, acetate, p-toluenesulfonate and the like.

The anti-obesity effective dosage of active ingredient employed for the treatment of obesity may vary depending on the particular compound employed, the mode of administration and the severity of the condition being treated. However, in general, satisfactory results are obtained when the compounds of formula (I) are administered at a daily dosage of from about 2 milligrams to about 400 milligrams per kilogram of animal body weight, p.o., preferably given in divided doses two to four times a day, or in sustained release form. For most large mammals, the total daily dosage is from about 25 to about 1000 milligrams. Dosage forms suitable for internal use comprise from about 7.5 to about 500 milligrams of the active compound in intimate admixture with a solid or liquid pharmaceutically acceptable carrier or diluent.

A representative formulation suitable for oral administration two to four times a day for the treatment of obesity is a capsule prepared by standard encapsulating techniques which contains the following:

| INGREDIENTS | WEIGHT (mg.) |
|---|---|
| ($\pm$)-1-(3,7-dimethyloctyl)-2-phenylimidazole | 100 |
| inert solid diluent (starch, lactose, kaolin) | 200 |

EXAMPLE 1

($\pm$)-1-(3,7-dimethyloctyl)-2-phenylimidazole

To a solution of 21.5 g. (0.14 mole) of 2-phenylimidazole in 60 ml. dry dimethylformamide and 300 ml. dry tetrahydrofuran under nitrogen atmosphere there is added at room temperature 9.0 g. (0.19 mole) of 50% sodium hydride/mineral oil suspension. The resulting mixture is stirred and heated to 50° C. for about 3 hours. After cooling to room temperature the resulting mixture is treated dropwise with a solution of 40.5 g. (0.18 mole) of ($\pm$)-1-bromo-3,7-dimethyloctane in dry tetrahydrofuran. The reaction mixture is stirred over night at room temperature and the resulting mixture is filtered and the residue washed with tetrahydrofuran. The combined filtrate is concentrated in vacuo to an oil, the oil is then dissolved in methylene chloride, washed with water, dried over anhydrous sodium sulfate, filtered and concentrated in vacuo to yield an oily product. Distillation gave ($\pm$)-1-(3,7-dimethyloctyl)-2-phenylimidazole; b.p. 150° to 157° C. at 0.2–0.16 mm.

Following the above procedure and using in place of 2-phenylimidazole an equivalent amount of (a) 2-(p-fluorophenyl)imidazole, or
(b) 4-phenylimidazole there is obtained
(a) ($\pm$)-1-(3,7-dimethyloctyl)-2-(p-fluorophenyl) imidazole or (b) ($\pm$)-1-(3,7-dimethyloctyl)-4-phenyl imidazole b.p. 155° to 165° C. at 0.2 mm respectively.

Also following the above procedure and using in place of ($\pm$)-1-bromo-3,7-dimethyloctane an equivalent amount of (c) ($\pm$)-1-bromo-4,8-dimethylnonane, or
(d) ($\pm$)-1-bromo-5,9-dimethyldecane, there is obtained
(c) ($\pm$)-1-bromo-4,8-dimethylnonane, or
(d) ($\pm$)-1-bromo-5,9-dimethyldecane, there is obtained
(c) ($\pm$)-1-(4,8-dimethylnonyl)-2-phenylimidazole, or
(d) ($\pm$)-1-(5,9-dimethyldecyl)-2-phenylimidazole respectively.

Also following the above procedure and using in place 2-phenylimidazole an equivalent amount of 4-phenylimidazole and using in place of ($\pm$)-1-bromo-3,7-dimethyloctane an equivalent amount of ($\pm$)-1-bromo-5,9-dimethyldecane there is obtained (c) ($\pm$)-1-(5,9-dimethyldecyl)-4-phenylimidazole b.p. 195° to 205° C. at 0.5 mm.

The ($\pm$)-1-(3,7-dimethyloctyl)-2-phenylimidazole of this example is an effective anti-obesity agent when orally administered to an animal in need of said treatment at a dosage of 150 mg. two to four times a day.

What is claimed is:

1. A compound of the formula

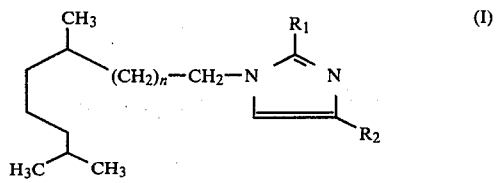

wherein $R_1$ and $R_2$ each represent hydrogen, or

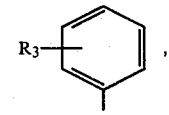

and $R_3$ is hydrogen or fluoro, and n is 1, 2 or 3, and provided that one of $R_1$ and $R_2$ is other than hydrogen or a pharmaceutically acceptable acid addition salt thereof.

2. A compound of claim 1 in free base form.

3. A compound of claim 1 in which $R_3$ represents hydrogen.

4. The compound of claim 1 which is ($\pm$)-1-(3,7-dimethyloctyl)-2-phenylimidazole.

5. The compound of claim 1 which is ($\pm$)-1-(5,9-dimethyldecyl)-2-phenylimidazole.

6. The compound of claim 1 which is ($\pm$)-1-(3,7-dimethyloctyl)-4-phenylimidazole.

7. The compound of claim 1 which is ($\pm$)-1-(5,9-dimethyldecyl)-4-phenylimidazole.

8. A method of treating obesity which comprises administering to a mammal in need of said treatment an antiobesity effective amount of a compound of claim 1.

9. A pharmaceutical composition for use in the treatment of obesity which comprises an anti-obesity effective amount of a compound of claim 1 and a pharmaceutically acceptable diluent or carrier therefor.

* * * * *